United States Patent [19]
Schmid

[11] Patent Number: 4,583,548
[45] Date of Patent: Apr. 22, 1986

[54] BIOELECTRIC ELECTRODE-ARRANGEMENT

[75] Inventor: Walter Schmid, Pfaffenhofen, Fed. Rep. of Germany

[73] Assignee: C. R. Bard, Inc., Murray Hill, N.J.

[21] Appl. No.: 594,202

[22] Filed: Mar. 28, 1984

[51] Int. Cl.⁴ ............................................. A61B 5/04
[52] U.S. Cl. ................................................. 128/639
[58] Field of Search ............... 128/639, 641, 643, 644, 128/783, 798, 802, 803

[56] References Cited

U.S. PATENT DOCUMENTS

| | | | |
|---|---|---|---|
| 3,137,291 | 6/1964 | Phipps et al. | 128/2.1 |
| 3,265,638 | 8/1966 | Goodman et al. | 252/518 |
| 3,420,223 | 1/1969 | Day et al. | 128/639 |
| 3,468,303 | 9/1969 | Mosier | 128/2.1 |
| 3,490,440 | 1/1970 | Mosier et al. | 128/2.1 |
| 3,574,305 | 4/1971 | Muhl | 128/2.1 |
| 3,669,110 | 6/1972 | Low et al. | 128/2.1 |
| 3,993,049 | 11/1976 | Kater | 128/2.06 |
| 4,375,219 | 3/1983 | Schmid | 128/639 |

FOREIGN PATENT DOCUMENTS

| | | | |
|---|---|---|---|
| 2838866 | 3/1979 | Fed. Rep. of Germany | 128/639 |
| 3136366 | 4/1983 | Fed. Rep. of Germany | 128/640 |

*Primary Examiner*—Lee S. Cohen
*Attorney, Agent, or Firm*—Trexler, Bushnell & Wolters, Ltd.

[57] ABSTRACT

A bioelectric electrode arrangement is comprised of an electrode piece consisting of a metal and/or an electrically conductive carbon containing material whereby one side of the electrode piece to be intended for the skin-contact contains an ionic-conductive contact-electrolyte layer. The contact-electrolyte layer contains an iodine ions-forming salt of a metal which is the same as also present at least in the interfacial regions of the electrode immediately adjacent to the contact-electrolyte layer.

7 Claims, 4 Drawing Figures

BIOELECTRIC ELECTRODE-ARRANGEMENT

BACKGROUND OF THE INVENTION

The invention deals with an arrangement of bioelectric electrodes comprised of an electrode material which may be connected to metallic conductor lines and which consists of an electrically conductive material containing a metal and/or carbon and of an ionic-conductive contact-electrolyte layer attached to one side of the electrode intended for a placing onto the skin.

Arrangements of bioelectric skin-contact-electrodes of this kind, have been known as for instance described in U.S. Pat. Nos. 3,987,055 and 3,933,049 as well as in "Medical Electronics", Oct. 1978, pp. 65-67. These electrodes are used for measuring biological potentials for instance in the fields of electrocardiography, electroencephalography, etc. and their functionality is based on electrochemical reaction taking place at the interfaces between the skin and an electrolyte at one side and between the electrolyte and an electron-conducting material on the other side. The materials from which the electrodes and the electrolytes are prepared, are to be selected in such a way to permit reversibility of the electrochemical reactions. A known electrode is prepared by using silver as the electrode material coated at its surface with silver chloride. A NaCl-gel is used as electrolyte.

The interfacial areas of the electrodes react as electrochemical half-cells. Consequently, in practical applications, with conventional electrode arrangements, substantial interference DC-voltages (offset voltages) are found superimposed over the bioelectrical signals. External, electrical compensation measures turn out to be very difficult since the interference voltages vary mostly considerably. Voltages externally applied to the electrode arrangement, will result in separations of charges and, therefore, in correspondingly high interference voltages which will only gradually decay after a relatively long recovery time.

In reference to conventional electrode arrangements, the electrolytes commonly used, will produce motion-dependent, variable artifact-voltages. Furthermore, the electrolytes used may also cause various skin irritations.

The objectives of the invention deal with the development of a bioelectric electrode assembly by which no or almost no interference voltage will interfere with the bioelectric signal. Moreover, the electrode arrangement is to be skin-compatible and is not to cause any skin irritations.

Starting from a bioelectric electrode arrangement as described above, the objectives have been achieved according to this invention whereby the contact-electrolyte layer and at least the adjacent areas of the electrode contain iodine ion-forming substances and/or whereby the contact-electrolyte layer contains an iodine ion-forming salt with a cation derived from the metal in the electrode material, present at least in the superficial areas adjacent to the contact-electrolyte layer.

The iodine containing substances of the contact-electrolyte layer have a disinfecting effect on the skin. The particular formation of the interfacial regions will assure low offset DC-voltages.

In regard to a preferred form of execution which may also be applied in electrode systems other than the described electrode arrangement, the base electrode consists of two areal opposed electrode layers of metal and/or of a carbon containing electrically conductive material whereby the two electrode layers are separated by an ionic-conductive electrolyte intermediate layer. The first electrode layer is attached to the connecting wires and the second electrode layer is coated at the opposite side away from the first electrode layer with a contact-electrolyte layer intended as the contacting surface with the skin. The electrolyte intermediate layer preferably containing also an iodine ion-forming substance and suitably having the same quantitative or at least the same qualitative composition as the contact-electrolyte layer, will assure a considerable reduction of the interference voltages of the electrode assembly. Besides, the fluctuations of the interference voltages are reduced. Furthermore, an electrode arrangement of this type has a relatively low AC-impedance and the recovery time, for instance after a simulated defibrillation, is relatively short with this type of electrode.

The electrode layers are preferably to contain the same metal in each layer, for instance silver, zinc or copper. In general, metals with an atomic weight of at least 51 are suitable. The intermediate electrolyte layer is preferably to contain a salt of this metal; more specifically, an iodine ion-forming salt of this metal. Therefore, bioelectric currents will be able to affect a reversible motion of the metal ions between the two electrode layers as well as a motion in both directions of the iodine ions between the second electrode layer and the two electrolyte layers. This will result in extremely low and negligibly fluctuating offset DC-voltages.

The intermediate electrolyte layer and the contact-electrolyte layer may have a liquid or gel-like consistency. These electrolyte layers may be absorbed in carrier substrates, such as absorbing paper or fleece or similar materials. The electrolyte layers, in particular the contact-electrolyte layer, may also be in a solid form. In this case, the powdery components of the electrolyte layers are mixed and pressed or sintered under high pressure. The use of solid electrolyte facilitates the handling of the electrode assembly.

Materials useful as iodine ion-forming substances are for instance iodides, in particular iodides of the metals used in the electrode layers, or triiodomethane ($CHI_3$). For the purpose of minimizing a polarization of the electrode, germanium or a tungstate of the metals used in the electrode layers may be added to the electrolyte layers.

For the purpose of reducing the transfer resistance at the interfaces, salts of the metals used in the electrode layers may be added to the electrode layers. Suitable salts are in particular the iodides and selenides of these metals.

In regard to the quantitative composition of the electrode layers and the electrolyte layers, it is important that the major component by weight in the electrode layers is the metal, for instance silver, zinc or copper, while the major component by weight in the electrolyte layers is the iodine ion-forming substance.

The principle described in the foregoing whereby an intermediate electrolyte layer is placed between two electrode layers, may not only be applied if a solid contact-electrolyte layer is present but also in the presence of a gel-like contact-electrolyte provided that this electrolyte is capable of forming iodine ions.

Another form of execution deals with an electrode assembly whereby the electrodes contain carbon in the form of graphite or carbon black as the electrically conductive component. The carbon may be blended and molded with a synthetic resin, for instance an epoxy resin. Conventional electrode assemblies of this kind exhibit also very high offset DC-voltages. According to this invention, the offset DC-voltage can also be substantially lowered if an iodine ion producing substance, in particular triiodomethane ($CHI_3$), is admixed to the carbon. Other suitable substances are metal iodides or iodo acetate $I(CH_3CO_2)_3$ or iodo perchlorate. Suitable substances for the contact-electrolyte layer, are iodides as for instance zinc iodide or copper iodide as gels or also in solid forms. Also suitable are potassium iodide or calcium iodide.

In the following, some execution examples of the invention shall be explained in more detail by referring to the attached drawings.

Figure 1:
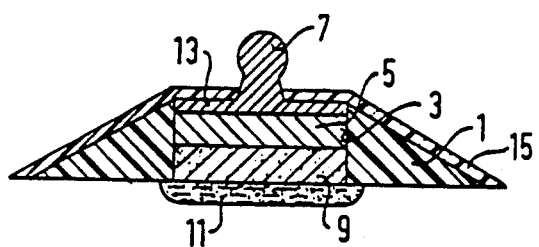
FIG. 1 illustrates the first form of execution of an electrode arrangement utilzing an electrolyte gel.

The electrode arrangement shown in FIG. 1 consists of an insulating plastic casing 1 in which a metal plate 5 is enclosed in opening 3. The metal plate 5 consists of zinc. At the side opposite of the connector terminal 7, the metal plate 5 is attached to a solid electrolyte layer 9. This solid electrolyte layer 9 consists of a zinc iodide plate which has been pressed or sintered from zinc iodide powder and pressed together with the metal plate 5. The other side of the solid electrolyte layer 9 away from the metal plate 5 forms the skin-contact side of the electrode and is, during the application, to be coated with an electrogel 11 also consisting of zinc iodide. Instead of zinc, the metal plate may also consist of silver or copper, in which case the electrolyte layer 9 is prepared from silver iodide or copper iodide, respectively. As contact-gel 11, a gel of silver iodide, potassium or copper iodide is most suitably used. The connector terminal 7 is the raised part of a connecting base plate 13 which is in contact with the metal plate 5 covering the surface opposite to the solid electrolyte layer 9. A heat-sealable plastic 15 covers the connecting base plate 13 and the adjacent areas of the casing 1.

Figure 2:
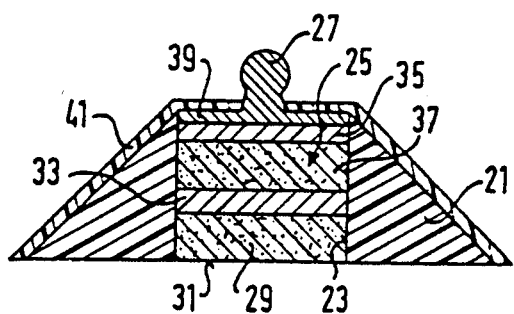
FIG. 2 shows a second form of execution of an electrode arrangement with a solid contact-electrolyte layer.

FIG. 2 illustrates another form of execution of a bioelectric electrode arrangement with a casing 21 of an insulating plastic material. This casing has a cut-out section 23 containing the electrodes generally labeled with 25. At one side of the electrodes, a metallic connecting terminal 27 is attached by which the electrodes will be connected to the instrument measuring the bioelectric signals, for instance to an electrocardiograph. At the other side, opposite to the connecting terminal 27, the electrodes 25 are attached to an electrolyte layer 29 consisting of a solid electrolyte material which shall be further described below. The outer surface 31 of the electrolyte layer 29 facing away from the electrodes 25, is freely accessible and is intended for a placing onto the skin. The electrodes 25 consist of two electrode layers 33 and 35 which are separated from each other by an electrolyte layer 37 also consisting of a solid electrolyte material. The electrode layers 33, 35 are in an areal or flush contact with the electrolyte layer 37. The electrode layer 33 connects the electrolyte layers 29 and 37. The electrolyte layer 37 is in an areal contact with electrode layer 35 which is in turn connected to the base plate 39. A heat-sealable foil 41 covers the connecting base plate 39 as well as the adjacent areas of the casing 21.

The electrode layers 33 and 35 consist predominantly of metal to which additives may be admixed capable of forming ions as further discussed below. The electrolyte layers 29 and 37 consist predominantly of an iodine ion-forming salt of the metal present in the electrode layers, in particular of the iodide of this metal, but other additives may also be admixed to the electrolyte layers. Both electrolyte layers 29, 37 are prepared by pressing or sintering the powdery, solid starting materials. Subsequently, the electrolyte layers are pressed together with the electrode layers 33, 35.

Suitable examples of the compositions of the electrode and electrolyte layers are as follows:

EXAMPLE 1

Electrolyte layers 29, 37:
Silver iodide: 62.7 weight %
Silver tungstate: 19.8 weight %
Germanium: 17.5 weight %
Electrode layer 35:
Silver: 50 weight %
Silver iodide: 50 weight %
Electrode layer 33:
Silver: 82.3 weight %
Silver selenide: 17.7 weight %

EXAMPLE 2

Electrolyte layers 29, 37:
Silver iodide: 69 weight %
Silver tungstate: 10 weight %
Germanium: 10 weight %
Iodoform: 11 weight %
Electrode layer 35:
Silver: 100 weight %
Electrode layer 33:
Silver: 100 weight %

EXAMPLE 3

Electrolyte layers 29, 37:
Silver iodide: 100 weight %
Electrode layer 35:
Silver: 100 weight %
Electrode layer 33:
Silver: 100 weight %

EXAMPLE 4

Electrolyte layers 29, 37:
Silver iodide: 80 weight %
Silver tungstate: 20 weight %
Electrode layer 35:
Silver: 80 weight %
Iodoform: 20 weight %
Electrode layer 33:
Silver: 90 weight %
Silver selenide: 10 weight %

EXAMPLE 5

Electrolyte layers 29, 27:
Zinc iodide: 66 weight %
Zinc tungstate: 19 weight %
Germanium: 15 weight %
Electrode layer 35:
Zinc: 60 weight %

Zinc iodide: 40 weight %
Electrode layer 33:
Zinc: 88 weight %
Zinc selenide: 12 weight %

EXAMPLE 6

Electrolyte layers 29, 37:
Zinc iodide: 100 weight %
Electrode layer 35:
Zinc: 100 weight %
Electrode layer 33:
Zinc: 100 weight %

In examples 1, 4 and 5, the electrode layers 33, 35 have a different composition. Although the described sequence is preferred, the sequence of the electrode layers 33, 35 may also be reversed.

Figure 3:
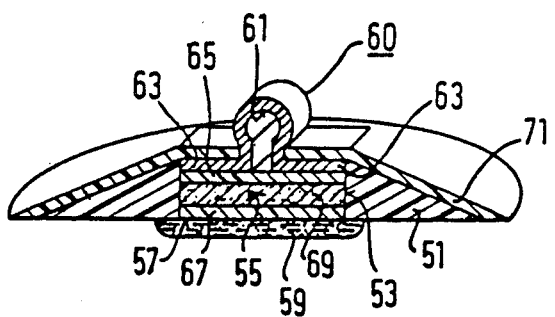
FIG. 3 shows a third form of execution utilizing a contact-electrolyte gel in the electrode arrangement.

FIG. 3 shows yet another form of execution of a bioelectric electrode which is characterized by its simple and economical design. The electrode assembly consists again of a casing 51 made of an insulating material, having an opening 53 for taking up the combined electrode pieces labeled with 55. The one side 57 of the electrode pieces intended for the skin-contact is freely accessible and will be coated during the application with an electrolyte layer 59 consisting, for instance, of a gel-like contact-electrolyte. The other opposite side of the electrode pieces 55 contains the contact element 60 shaped as a bow for connecting a plug of an instrument measuring the bioelectrical signals. The contact element 60 consists of a strip of a sheet-metal bended to form a bow-shaped receptacle 61 above the casing 51 into which the connecting terminal of the measuring instrument can be inserted. Both ends 63 of the bended sheet-metal are bent outwards in the same plane and along an edge parallel to the length-axis of the receptacle 61. Both ends or shanks 63 lay flat on the electrode pieces 55. The electrode pieces 55 consist of two electrode layers 65, 67 placed a distance apart and separated by an electrolyte layer 69. This electrolyte layer 69 consists of a non-conductive carrier substrate, not further specified in this case, consisting for instance of paper or a synthetic fleece or a similar material impregnated by the actual non-ionic conductive electrolyte material.

In the illustrated execution example, the electrode layers 65, 67 consist of a metal, preferably zinc, and the electrolyte material consists of a salt of this metal, preferably the iodide capable of producing iodine ions. In the execution example illustrated in FIG. 3, the electrolyte material 69 consists of zinc iodide. Analogously, silver or copper, etc. may also be used as the electrode material in which case the electrolyte material will consist of silver- or copper iodide, respectively. The gel forming electrolyte layer 59 is to contain also the iodide of the electrode material, which means zinc iodide or silver- or copper iodide, respectively, or also potassium- or calcium iodide.

In reference to the preparation of the electrode piece 55, the carrier substrate layer is saturated with a solution of the electrolyte material, such as zinc iodide, and subsequently dried. Then, both sides of the carrier material are coated with a liquid zinc dispersion. After drying, the coated zinc dispersion forms the electrode layers. The electrode piece 55, together with the connecting element 60, is placed into the casing 51 and fastened in this position by a heat-sealable foil 71 which covers the shanks 63 and the adjacent areas of the casing 51.

The foil 71 may cover the entire casing 51 from all sides in this example as well as in the other illustrated forms of execution, reaching even in the contacting surface of the electrode piece 55 whereby the sidewalls of the electrodes are also sealed.

The materials and compositions described in the examples of the electrode arrangement according to FIG. 2 may also be used in an electrode arrangement according to FIG. 3. The electrolyte materials of these examples may be dispersed in a base carrier gel. Furthermore, for the preparation of solid electrolytes, a carrier substrate may also be used in which the electrolyte materials are incorporated.

Figure 4:
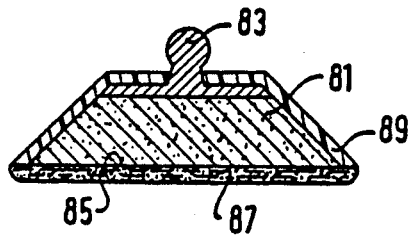
FIG. 4 illustrates an electrode arrangement with carbon electrodes.

FIG. 4 shows yet another execution form of a bioelectric electrode assembly with an essentially disc-shaped electrode piece 81 having a connecting element 83 formed, for instance, as a terminal post attached to the topside of the unit for the connection with an instrument measuring bioelectric signals. The other side of the unit 85 intended for a skin-contact is to be coated during the application with an electrolyte layer 87, for instance an electrolyte gel. The electrode piece 81 consists of graphite or electrically conductive carbon black blended with an iodine ion-forming substance preferably consisting of triiodomethane (CHI$_3$) whereby the electrode is shaped into its form by sintering under pressure or by casting in the presence of an epoxy binder. The electrolyte layer 87 contains also iodine ion-forming substances, in particular an iodide such as zinc iodide, silver iodide, copper iodide, potassium iodide or calcium iodide.

The connecting element 83 consists of a metal piece or a molded carbon piece which is fastened to the electrode 81 by a heat-sealable foil 89. Alternatively, the connecting element may consist of the same electrically conductive material as the electrode 81 and electrode and connecting element may be formed as a single piece.

In regard to the preparation of the electrode piece 81, the following composition is preferably used.

50 weight %: graphite
17 weight %: iodine-carbon
8 weight %: iodoform (CHI$_3$)
17 weight %: epoxy resin (base)
8 weight %: epoxy hardener For the purpose of improving the strength, a part of the epoxy resin may be replaced by carbon fibers. In regard to the employed iodine-carbon, the material is a granulated active carbon having, for instance, 5 to 6 weight % elemental iodine absorbed.

If the electrode 81 is formed by a pressure-sintering process, carbon fibers may also be added if desired for improving the mechanical strength and also the conductivity. In regard to the aforementioned composition, the epoxy resin may be replaced by another binder whereby different weight-fractions of binder may be chosen.

The mixture of graphite, iodine-carbon and iodoform may also be dissolved and/or dispersed in a lacquer-type binder which is coated and layered on the surface of a conductive connecting element, again preferably consisting of carbon, and then dried.

I claim:
1. A bioelectric electrode assembly comprising an electrode piece and an ionically conductive contact electrolyte layer as a coating on said electrode piece,
    said electrode piece comprising an electrically conductive material selected from the group consisting of electrically conductive carbon black, electrically conductive graphite, and mixtures thereof, and triiodomethane blended therewith, said ionically conductive contact electrolyte layer being in electrically conductive contact with said electrode piece an adapted for placing onto the skin to establish electrically conductive contact therewith, an iodine ion forming substance distributed throughout said contact electrolyte layer, said iodien ion forming substance being an iodide salt selected from the goup consisting of zinc iodine, silver iodide, copper iodide, potassium iodide, calcium iodide, and mixtures thereof.

2. An electrode assembly as set forth in claim 1 wherein said electrode piece constitutes a sintered mass of said conductive material and said triiodomethane.

3. The structure as set forth in claim 2 and furthe comprising carbon fibers distributed through said sintered mass for enhancing conductivity and for enhancing the strength of said sintered mass.

4. An electrode assembly as set forth in claim 1 and further comprising a binder, and wherein said binder is distributed throughout said conductive material of said electrode piece for enhancing the mechanical strength thereof.

5. The structure as set fourth in claim 4 and further comprising carbon fibers distributed throughout said binder.

6. The electrode assembly as set forth in claim 1 wherein said electrode piece is shaped to include a terminal post integrally formed with as a part of said piece.

7. The electrode assembly as set forth in claim 1 and further comprising a terminal post for connection to an instrument for measuring bioelectric signals, and a heat-sealable foil securing said terminal post to said electrode piece in electrical contact therewith.

* * * * *